(12) United States Patent
Kondo et al.

(10) Patent No.: US 11,782,172 B2
(45) Date of Patent: Oct. 10, 2023

(54) SCINTILLATOR ARRAY, METHOD FOR MANUFACTURING SCINTILLATOR ARRAY, RADIATION DETECTOR, AND RADIATION INSPECTION DEVICE

(71) Applicants: KABUSHIKI KAISHA TOSHIBA, Tokyo (JP); TOSHIBA MATERIALS CO., LTD., Yokohama (JP)

(72) Inventors: Hiroyasu Kondo, Yokohama (JP); Yukihiro Fukuta, Yokohama (JP); Kazumitsu Morimoto, Yokohama (JP); Makoto Hayashi, Chigasaki (JP)

(73) Assignees: Kabushiki Kaisha Toshiba, Tokyo (JP); Toshiba Materials Co., Ltd., Yokohama (JP)

( * ) Notice: Subject to any disclaimer, the term of this patent is extended or adjusted under 35 U.S.C. 154(b) by 0 days.

(21) Appl. No.: 17/660,861

(22) Filed: Apr. 27, 2022

(65) Prior Publication Data

US 2022/0260731 A1 Aug. 18, 2022

Related U.S. Application Data

(63) Continuation of application No. PCT/JP2020/042172, filed on Nov. 12, 2020.

(30) Foreign Application Priority Data

Nov. 13, 2019 (JP) .................................. 2019-205706

(51) Int. Cl.
*G01T 1/20* (2006.01)
*G01T 1/203* (2006.01)

(52) U.S. Cl.
CPC .......... *G01T 1/2002* (2013.01); *G01T 1/2033* (2013.01)

(58) Field of Classification Search
CPC .......................... G01T 1/2002; G01T 1/2033
See application file for complete search history.

(56) References Cited

U.S. PATENT DOCUMENTS

| 5,636,299 | A | * | 6/1997 | Bueno | ................. G01T 1/20185 250/367 |
|---|---|---|---|---|---|
| 5,866,908 | A | | 2/1999 | Novak | |

(Continued)

FOREIGN PATENT DOCUMENTS

| JP | H09-292469 A | 11/1997 |
|---|---|---|
| JP | 2002-311142 A | 10/2002 |

(Continued)

OTHER PUBLICATIONS

International Search Report and Written Opinion (Application No. PCT/JP2020/042172) dated Dec. 28, 2020 (with English translation).

*Primary Examiner* — Hugh Maupin
(74) *Attorney, Agent, or Firm* — BURR PATENT LAW, PLLC

(57) ABSTRACT

A scintillator array includes: a structure having scintillator segments and a first reflective layer, the first reflective layer being provided between the scintillator segments and being configured to reflect light, and the scintillator segments having a sintered compact containing a rare earth oxysulfide phosphor; and a layer having a second reflective layer provided above the structure, the second reflective layer being configured to reflect light. The first reflective layer has a portion extending into the layer.

11 Claims, 7 Drawing Sheets

(56) References Cited

U.S. PATENT DOCUMENTS

| | | | | |
|---|---|---|---|---|
| 2008/0290296 A1* | 11/2008 | Tahon | ............... | C09K 11/7744 |
| | | | | 250/484.4 |
| 2014/0301527 A1* | 10/2014 | Morimoto | ............. | G01T 1/2002 |
| | | | | 250/367 |
| 2018/0188386 A1 | 7/2018 | Kondo et al. | | |
| 2018/0188387 A1 | 7/2018 | Morimoto et al. | | |
| 2019/0324158 A1* | 10/2019 | Shindou | ............... | A61B 6/4208 |

FOREIGN PATENT DOCUMENTS

| | | |
|---|---|---|
| JP | 2015-049126 A | 3/2015 |
| JP | 2017-037096 A | 2/2017 |
| WO | 2017/082337 A1 | 5/2017 |
| WO | 2017/110850 A1 | 6/2017 |

\* cited by examiner ured examples of the scintillator array according to the embodiment.

SCINTILLATOR ARRAY, METHOD FOR MANUFACTURING SCINTILLATOR ARRAY, RADIATION DETECTOR, AND RADIATION INSPECTION DEVICE

CROSS-REFERENCE TO RELATED APPLICATIONS

This application is a continuation of prior International Application No. PCT/JP2020/042172 filed on Nov. 12, 2020; the entire contents of all of which are incorporated herein by reference.

FIELD

Embodiments described herein generally relate to a scintillator array, a method for manufacturing the scintillator array, a radiation detector, and a radiation inspection device.

BACKGROUND

A radiation inspection device such as an X-ray tomograph (hereinafter, referred to as an X-ray CT scanner) is used for inspection in various fields such as medical diagnosis and industrial nondestructive inspection. The X-ray CT scanner includes an X-ray tube (X-ray source) and an X-ray detector, the X-ray tube being capable of irradiating fan-beam X-rays, the X-ray detector having a plurality of X-ray detection elements, and the X-ray tube and the X-ray detector being disposed on the opposite side of a tomographic surface of an inspection target from each other.

The X-ray CT scanner irradiates fan-beam X-rays from the X-ray tube to the inspection target while rotating around the inspection target, and collects X-ray absorption data based on X-ray through the inspection target with the X-ray detector. Then, the X-ray absorption data is analyzed by a computer to form a tomogram.

A radiation detector in the X-ray CT scanner widely uses detection elements using a solid scintillator. The radiation detector equipped with the detection elements using the solid scintillator can further increase resolution of the X-ray CT scanner and other devices because it is easy to downsize the detection elements and increase the number of channels.

The X-ray CT scanner and other radiation inspection devices are used in various fields such as medical and industrial applications. Examples of the X-ray CT scanner include a multi-slice device, which is formed by arranging the detection elements such as photodiodes on a two-dimensional array vertically and horizontally and then mounting a scintillator array onto the arranged detection elements. The multi-slice device can overlay computed tomography (CT) images to form a three dimensional CT image.

The radiation detector of the radiation inspection device includes a plurality of detection elements arranged in multiple vertical and horizontal rows, and each detection element has a scintillator segment. The radiation detector converts X-rays incident on the scintillator segments into visible light and converts the visible light into electrical signals by the detection elements to form an image. In recent years, the detection elements have been made smaller and a pitch between adjacent detection elements has been made narrower to obtain high resolution. These causes downsizing of the scintillator segment.

Among various scintillator materials used for the scintillator segment as described above, rare earth oxysulfide-based phosphor ceramics have high luminous efficiency and suitable characteristics for use in the scintillator segment. For this reason, radiation detectors combining scintillator segments each processed by cutting or grooving from a sintered compact (ingot) of rare earth oxysulfide-based phosphor ceramics, which are the scintillator materials, and photodiodes as the detection elements are becoming popular.

Examples of the scintillator using phosphor ceramics include a scintillator made of a sintered compact of a gadolinium oxysulfide phosphor. The scintillator array using the above scintillator is manufactured, for example, as follows. First, rare earth oxysulfide-based phosphor powder, which is the scintillator material, is molded into an appropriate shape and sintered to form a sintered compact (ingot). The sintered compact is then subjected to a cutting process such as cutting or grooving to form scintillator segments corresponding to a plurality of detection elements. Furthermore, a reflective layer that reflects light is formed between these scintillator segments and integrated to manufacture a scintillator array.

When the scintillator array is used in the radiation detector, dimensional accuracy of the scintillator array affects the resolution of CT diagnostic images. Furthermore, the radiation detector in the X-ray CT scanner is subjected to a temperature of 50° C. or more and 60° C. or less at most. The scintillator array with a reflective layer containing resin can expand the reflective layer due to temperature rise and shrink the reflective layer due to temperature drop, resulting in minute dimensional changes between adjacent scintillator segments, that is, variation or the like in external dimensions mainly due to pitch shift of the scintillator segments, and warpage of the scintillator array. Such warpage and variation in external dimensions cause non-uniformity in an adhesive layer thickness between the scintillator array and a diode array when the scintillator array is bonded to the diode array, which is the detector, and deteriorate the resolution of the diagnostic images of the radiation detector. As the resolution of the diagnostic images of the radiation detectors becomes higher and higher, there is a need for a scintillator array with less warpage and variation in external dimensions. Furthermore, uniformity of the adhesive layer between the scintillator array and the diode array is becoming more and more important as a detection area of the radiation detector becomes finer.

DETAILED DESCRIPTION

Figure 1:
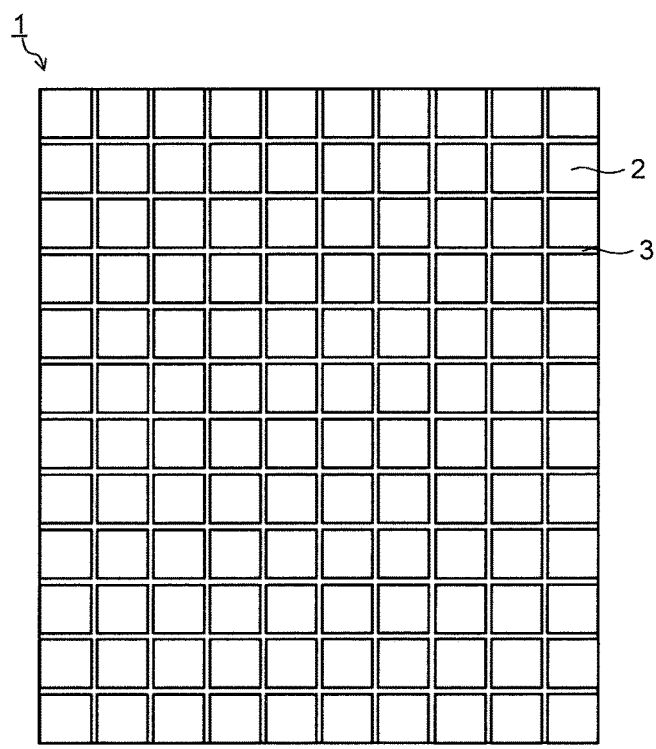
FIG. 1 is a plan view illustrating a structural example of a scintillator array according to an embodiment.

A scintillator array according to an embodiment includes: a structure having scintillator segments and a first reflective layer, the first reflective layer being provided between the scintillator segments and being configured to reflect light, and the scintillator segments having a sintered compact containing a rare earth oxysulfide phosphor; and a layer having a second reflective layer provided above the structure, the second reflective layer being configured to reflect light. The first reflective layer has a portion extending into the layer.

Hereinafter, embodiments of the present invention will be explained with reference to the drawings. A relationship between a thickness and planar dimension of each component, a thickness ratio among the components illustrated in the drawings, and so on may be different from actual ones. Further, in the embodiments, substantially the same components are denoted by the same reference signs and a description thereof may be partly omitted.

A scintillator array, a radiation detector, and a radiation inspection device according to an embodiment are described below.

(Scintillator Array)

Figure 2:
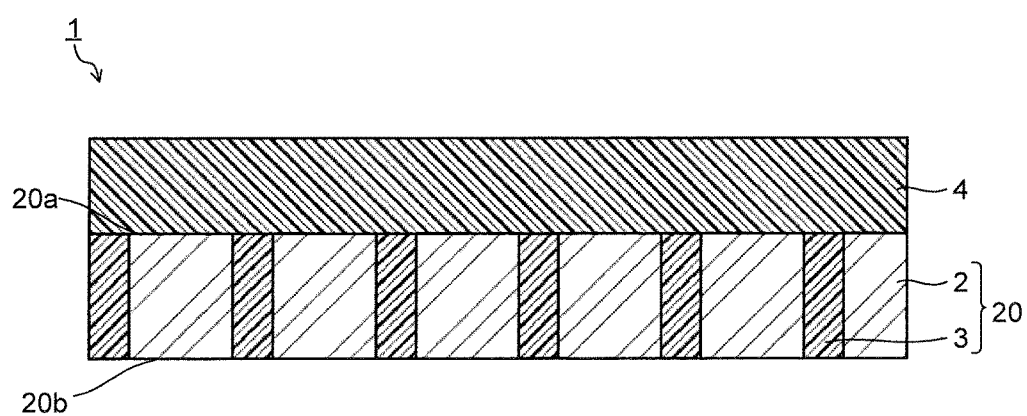
FIG. 2 is a cross-sectional view illustrating a structural example of a conventional scintillator array.
Figure 3:
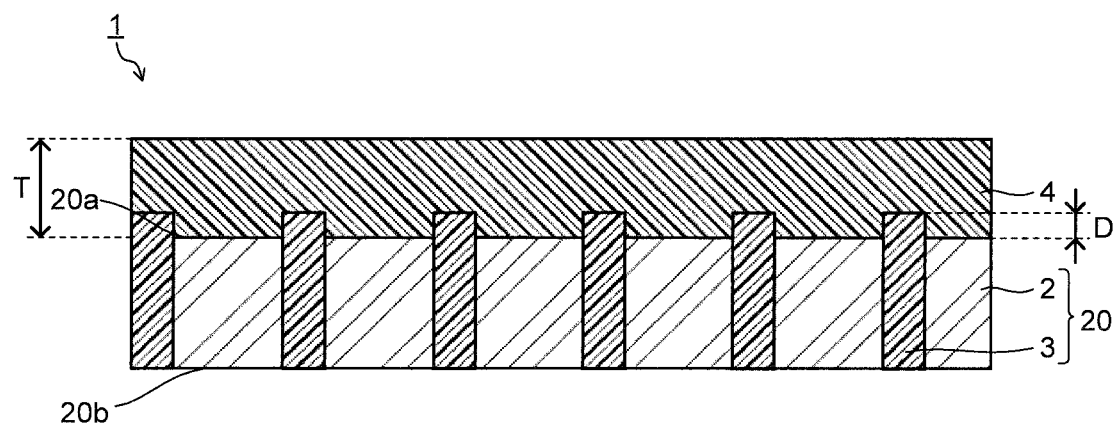
FIG. 3 is a cross-sectional view illustrating the structural example of the scintillator array according to the embodiment.
Figure 4:
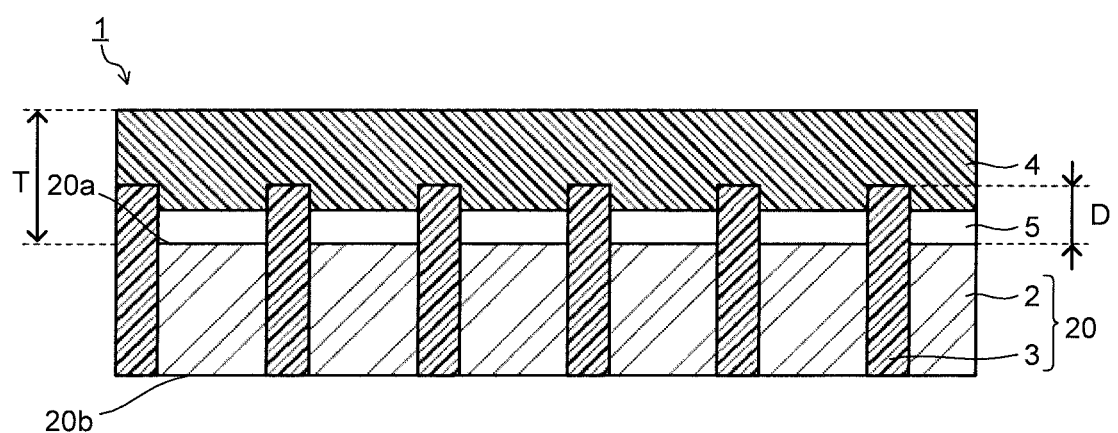
FIG. 4 is a cross-sectional view illustrating another structural example of the scintillator array according to the embodiment.
Figure 5:
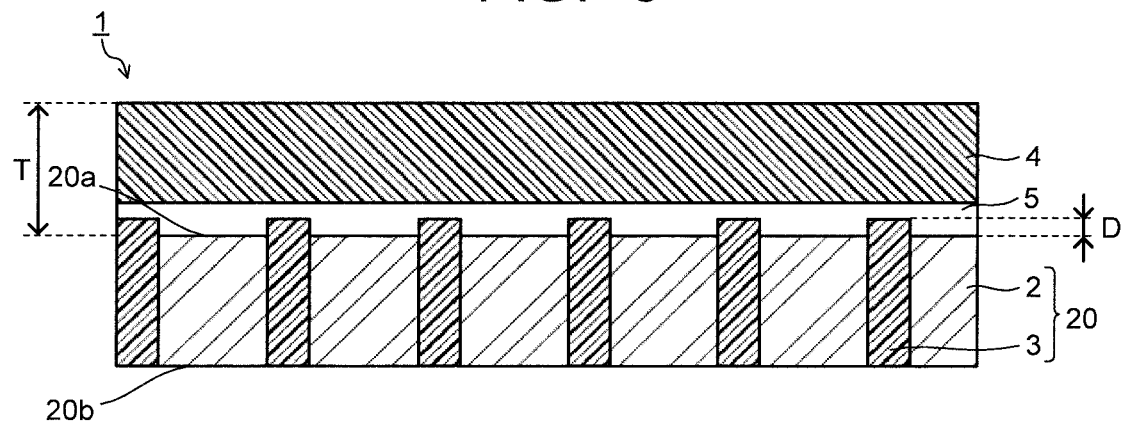
FIG. 5 is a cross-sectional view illustrating still another structural example of the scintillator array according to the embodiment.
Figure 6:
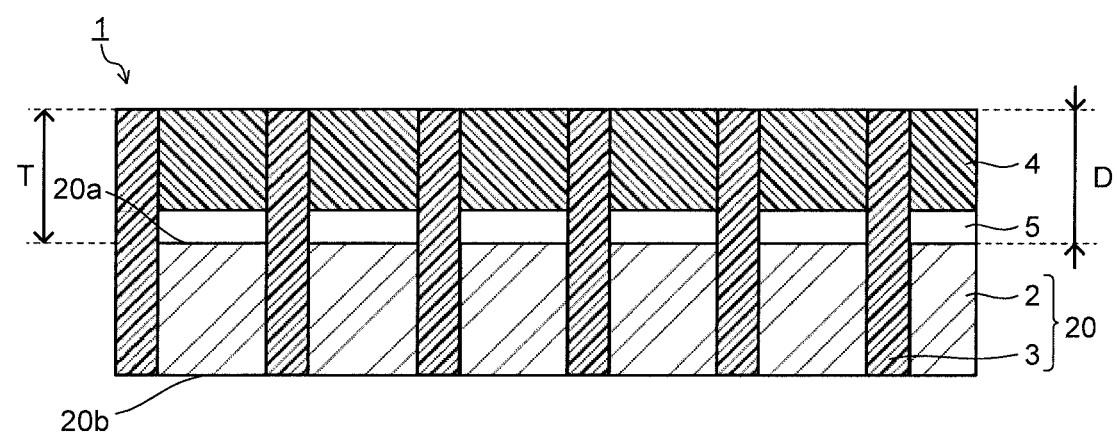
FIG. 6 is a cross-sectional view illustrating still another structural example of the scintillator array according to the embodiment.

FIG. 1 is a plan view illustrating a structural example of a scintillator array of the embodiment. FIG. 2 is a cross-sectional view illustrating a structural example of a conventional scintillator array. FIG. 3 is a cross-sectional view illustrating the structural example of the scintillator array of the embodiment. FIG. 4, FIG. 5, and FIG. 6 are cross-sectional views each illustrating another structural example of the scintillator array of the embodiment. FIG. 1 to FIG. 6 each illustrate a scintillator array 1, scintillator segments 2, a reflective layer 3, and a reflective layer (top reflective layer) 4. The reflective layer 4 is omitted in FIG. 1 for convenience.

The scintillator array 1 includes the scintillator segments 2, the reflective layer 3, and the reflective layer 4. The scintillator segments 2 and the reflective layer 3 form a structure 20 having a surface 20a, which is an X-ray incident surface, and a surface 20b on an opposite side of the surface 20a. The number of scintillator segments 2 is set appropriately according to a structure, resolution, and the like of a radiation detector.

In the conventional scintillator array, the surface 20a extends flatly from the scintillator segments 2 to the reflective layer 3, as illustrated in FIG. 2. On the other hand, in an example of the scintillator array of the embodiment, the reflective layer 3 partially enters into the reflective layer 4 to encroach thereon in a cross-section of the scintillator array 1 in a thickness direction, as illustrated in FIG. 3. In other words, the reflective layer 3 has a portion that extends into the reflective layer 4.

In another example of the scintillator array of the embodiment, the reflective layer 4 is bonded to the surface 20a via an adhesive layer 5 and the reflective layer 3 may partially enter into the reflective layer 4 to encroach thereon through the adhesive layer 5 in the cross-section of the scintillator array 1 in the thickness direction, as illustrated in FIG. 4. In other words, the reflective layer 3 has a portion that extends into the reflective layer 4 via the adhesive layer 5.

In still another example of the scintillator array of the embodiment, the reflective layer 4 is bonded to the surface 20a via the adhesive layer 5 and the reflective layer 3 may partially enter into the adhesive layer 5 to encroach thereon and not enter into the reflective layer 4 in the cross-section of the scintillator array 1 in the thickness direction, as illustrated in FIG. 5. In other words, the reflective layer 3 has a portion that extends into the adhesive layer 5 and does not extend to the reflective layer 4.

In still another example of the scintillator array of the embodiment, the reflective layer 4 is bonded to the surface 20a via the adhesive layer 5 and a part of the reflective layer 3 may penetrate the reflective layer 4 in the cross-section of the scintillator array 1 in the thickness direction, as illustrated in FIG. 6.

The scintillator segment 2 converts incident radiation rays (X-rays) into light (visible light). The scintillator segments 2 are integrated by the reflective layer 3 adhered thereto to form the structure 20.

The reflective layer 3 reflects light (visible light). The reflective layer 3 may transmit X-rays. The reflective layer 3 is provided between adjacent scintillator segments 2 and adheres to each scintillator segment 2.

The reflective layer 4 reflects light (visible light). The reflective layer 4 may transmit X-rays. For example, as illustrated in FIG. 3, the reflective layer 4 is provided above the surface 20a and covers the structure 20.

The scintillator array 1 may have either a structure where the scintillator segments 2 are arranged in a row or a structure where the scintillator segments 2 are arranged in a two-dimensional manner with the predetermined number of scintillator segments 2 in vertical and horizontal directions as illustrated in FIG. 1. When the scintillator segments 2 are two-dimensionally arranged, the reflective layer 3 is provided between the scintillator segments 2 arranged in the vertical direction and between the scintillator segments 2 arranged in the horizontal direction. The reflective layer 3 may surround the scintillator segments 2 along the surface 20a.

The scintillator segment 2 has a sintered compact containing a rare earth oxysulfide phosphor. Examples of the rare earth oxysulfide phosphor include the rare earth oxysulfide phosphor containing praseodymium (Pr) as an activator. Examples of rare earth oxysulfide include yttrium (Y), gadolinium (Gd), lanthanum (La), lutetium (Lu), and other oxysulfides of rare earth elements.

The rare earth oxysulfide phosphor preferably has a composition represented by

A general formula RE$_2$O$_2$S:Pr     (1)

(in the formula, RE denotes at least one element selected from the group consisting of Y, Gd, La, and Lu)

Among the rare earth elements mentioned above, Gd, in particular, has a large X-ray absorption coefficient and contributes to improvement of light output of the scintillator array 1. Therefore, the scintillator segment 2 more preferably has a Gd$_2$O$_2$S:Pr phosphor (GOS phosphor). Part of Gd may be substituted by other rare earth elements. At this time, a substitution amount of Gd by other rare earth elements is preferably 10 mol % or less.

That is, the rare earth oxysulfide phosphor preferably has a composition substantially represented by

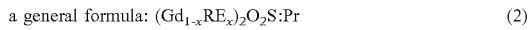

a general formula: (Gd$_{1-x}$RE$_x$)$_2$O$_2$S:Pr     (2)

(in the formula, RE denotes at least one element selected from the group consisting of Y, La, and Lu, and x is a number (atomic ratio) satisfying $0 \leq x \leq 0.1$).

The scintillator segment 2 may contain praseodymium (Pr) as the activator to increase the light output. Pr can reduce afterglow compared to other activators. Therefore, rare earth oxysulfide phosphor ceramics containing Pr as the activator is effective as a fluorescence generator for a radiation detector.

A content of Pr in the rare earth oxysulfide phosphor is preferably 0.001 mol % or more and 10 mol % or less of a content of a phosphor host (for example, $RE_2O_2S$ such as $Gd_2O_2S$). When the content of Pr is larger than 10 mol %, the light output may decrease. When the content of Pr is less than 0.001 mol %, an effect as a main activator cannot be sufficiently obtained. The content of Pr is more preferably 0.01 mol % or more and 1 mol % or less.

The rare earth oxysulfide phosphor may contain a small amount of at least one element selected from the group consisting of cerium (Ce), zirconium (Zr), and phosphorus (P) as a coactivator in addition to Pr as the main activator. These elements are effective in preventing exposure deterioration, afterglow, and the like. A total amount of these coactivators is preferably in a range of 0.00001 mol % or more and 0.1 mol % or less of the phosphor host.

A sintered compact constituting the scintillator segment 2 is preferably made of high-purity rare earth oxysulfide-based phosphor ceramics (scintillator material). Since impurities become a cause of a decrease in sensitivity of the scintillator, it is preferable to reduce as much as possible the impurity amount. In particular, since a phosphate radical ($PO_4$) becomes the cause of the decrease in sensitivity, its content is preferably 100 ppm or less. In the case of using fluoride or the like as a sintering aid for densification of the sintered compact, the sintering aid remains as an impurity, causing the decrease in sensitivity.

The sintered compact has a cube shape or a rectangular parallelepiped shape. A volume of the scintillator segment 2 is preferably 1 $mm^3$ or less. Downsizing the scintillator segment 2 can obtain a detected image with higher definition. Each size of a length (L), breadth (S), and thickness (T) of the scintillator segment 2 is not always limited but is preferably 1 mm or less. When the volume of the scintillator segment 2 is 1 $mm^3$ or less, a width (W) of the reflective layer 3 can be made thinner to 100 μm or less, and further to 50 μm or less. However, the width (W) of 40 μm or more is preferable for the reflective layer 3, because the width of less than 40 μm makes the manufacturing process more complicated.

The reflective layer 3 contains a resin that transmits light (light transmissive resin) and reflective particles that are dispersed in the resin and reflect light. The resin includes at least one selected from the group consisting of epoxy resin, silicone resin, phenol resin, urea resin, melamine resin, polyester resin, polyurethane resin, and acrylic resin. For example, hydrogenated epoxy resin, epoxy silicone resin, and so on are preferred for the epoxy resin. The reflective particles include at least one selected from the group consisting of titanium oxide, aluminum oxide (alumina), barium sulfate, zinc oxide, zirconium oxide, and silicon oxide. Air bubbles contained in the resin may have function as the reflective particles.

The reflective layer 4 can be made of the same light transmissive resin and reflective particles as the reflective layer 3.

Regarding a ratio between the light transmissive resin and the reflective particles in the reflective layer 3 and reflective layer 4, a mass ratio of the light transmissive resin is preferably 15% or more and 60% or less, and a mass ratio of the reflective particles is preferably 40% or more and 85% or less. The sum of the mass ratio of the light transmissive resin and the mass ratio of the reflective particles is 100%. When the mass ratio of the reflective particles is less than 40%, the reflection efficiency of the reflective layer decreases and the reflection efficiency of the reflective layer with respect to light having a wavelength of 512 nm is likely to be lower than 90%. When the mass ratio of the reflective particles is larger than 85%, the reflection efficiency of the reflective layer does not change, but the mass ratio of the light transmissive resin relatively decreases, resulting in difficulty in stable solidification of the reflective layer.

When bonding the pre-fabricated reflective layer 4 to the surface 20a of the structure 20, the adhesive layer 5 contains at least one resin selected from the group consisting of epoxy resin, silicone resin, phenol resin, urea resin, melamine resin, polyester resin, polyurethane resin, polyolefin resin, and acrylic resin, and cured by light, heat, or moisture. The adhesive layer 5 may be a light transmissive resin, but the adhesive layer 5 preferably contains at least one selected from the group consisting of titanium oxide, zirconium oxide, aluminum oxide, and silicon oxide to reduce that the light from one scintillator segment 2 enters the other one scintillator segment 2 through the adhesive layer 5.

As described above, the scintillator array of the embodiment has a constitution in which the reflective layer 3 partially enters into the reflective layer 4 or the adhesive layer 5.

A scintillator used in a radiation inspection device such as an X-ray CT scanner confines light generated by X-rays within pixels using a reflective layer and efficiently extracts the light to a photodiode side. It is common to have a reflective layer that is formed to fill a space between the scintillator segments and, in some cases, a top reflective layer that is formed to further cover the scintillator array on an incident surface side of the X-rays as the reflective layer. The light from the scintillator emitted by X-rays is efficiently guided to the photodiode directly or through these reflective layers. The scintillator array incorporated in an X-ray detector is subjected to a temperature of 50° C. or more and 60° C. or less at most and is kept at room temperature when not in operation. The scintillator array is subjected to forces associated with high-speed rotation around an object to be inspected during operation. One of the problems that may be caused by variation of operating environmental temperature and internal stress caused by the rotation is that the top reflective layer is often peeled off from the scintillator array, and countermeasures are required.

To cope with this problem, a known technique prevents variation and distortion of light output between scintillator segments by selecting a color of the reflective particles contained in the epoxy resin and combining a resin with a glass transition point of the epoxy resin of 80° C. or more in the reflective layer between the scintillator segments.

A known scintillator array has the glass transition point of the light transmissive resin constituting the reflective layer of 50° C. or more, and a thermal expansion coefficient of the light transmissive resin at a temperature higher than the glass transition point of $3.5 \times 10^{-5}$/° C. or less. In general, the thermal expansion coefficient of the light transmissive resin changes significantly after the glass transition point, and the warpage caused by this change is adjusted by setting conditions.

Further, a known scintillator array has a constitution that the scintillator segments are integrated by the reflective layer, the glass transition point of the light transmissive resin of the reflective layer is 50° C. or more, and the glass transition point of the light transmissive resin of a second reflective layer disposed on an X-ray incident surface side of the scintillator segments is 30° C. or less to reduce the warpage of the scintillator array.

These scintillator arrays can improve warpage to some extent. However, when these scintillator arrays have a top reflective layer, these scintillator arrays may not be effective to peeling of the top reflective layer in the scintillator array to require their further improvement.

Materials used for the top reflective layer and the scintillator segments have a large difference in a linear expansion coefficient and an elastic modulus. This difference causes stress when the scintillator array is incorporated into a detector and exposed to the variation of operating environmental temperature and centrifugal force due to rotation, which can lead to peeling of the top reflective layer.

To deal with these issues, the scintillator array in this embodiment has the reflective layer 3 entering into the reflective layer 4 or the adhesive layer 5 to increase a contact area by these irregularities and to obtain a so-called anchor effect, which prevents the reflective layer 4 from peeling off.

Table 1 lists an example of a peeling occurrence rate in a compulsory test for each of the conventional scintillator array with the structure illustrated in FIG. 2 and the scintillator array with the structure illustrated in FIG. 3. In the compulsory test, the scintillator array is heated from room temperature to 50° C. in 5 minutes, left for 10 minutes, and then rotated at a rotation speed of 200 rpm for 5 minutes at room temperature. These operations are taken as one cycle of operation, and 100 cycles are performed for each sample. In the compulsory test of 100 prototype samples, there is no peeling in the scintillator array with the structure illustrated in FIG. 3, which indicates that peeling resistance is greatly improved.

TABLE 1

| Structure of scintillator array | Number of prototypes (pieces) | Number of occurrences of peeling (pieces) | Peeling occurrence rate (%) |
| --- | --- | --- | --- |
| FIG. 2 | 100 | 5 | 5 |
| FIG. 3 | 100 | 0 | 0 |

The scintillator array of the embodiment has the structure where the reflective layer 3 partially enters into the layer including the reflective layer 4, as illustrated in FIG. 3, FIG. 4, FIG. 5, and FIG. 6. However, a peeling prevention effect decreases as an entry length decreases. To achieve the effective peeling prevention effect, a ratio D/T of a length D of the portion of the reflective layer 3 extending into the layer including the reflective layer 4 to a thickness T of the reflective layer 4 or the reflective layer 4 and the adhesive layer 5 (the layer including the reflective layer 4) in a cross-section of the scintillator array 1 in a thickness direction is preferably in a range of 0.10 or more and 1.00 or less, more preferably in a range of 0.20 or more and 1.00 or less. The thickness T and length D can be measured from an observation image obtained by observing the cross-section of the scintillator array 1 in the thickness direction by an electron microscope or an optical microscope. Since the reflective layer 3, reflective layer 4, and adhesive layer 5 form a polymer network structure in each layer, an interface between these layers is clear. When a pigment concentration is different, it is even clearer, making it easier to determine the thickness T and length D.

Next, an example of a manufacturing method of the scintillator array 1 will be explained. The scintillator array 1 is manufactured as follows. Here, the case with the structure illustrated in FIG. 4 is explained as an example.

FIG. 7 to FIG. 10 are cross-sectional views to explain the method example of manufacturing the scintillator array of the embodiment. A first step is to form a white sheet of a predetermined size with epoxy resin or other resins containing a white reflective material.

The white sheet can be formed using materials such as a mixture of the reflective particles and light transmissive resin, or lacquer-based paint. The mixture of the reflective particles and light transmissive resin preferably has the same constitution as the reflective layer 3. The white sheet may be a commercially available white sheet.

The white sheet forms the reflective layer 4 and a thickness thereof is in a range of 50 μm or more and 250 μm or less. The thickness less than 50 μm cannot obtain a sufficient improvement effect of reflection efficiency of light. The thickness larger than 250 μm decreases a transmitted X-ray dose to decrease detection sensitivity.

Figure 7:
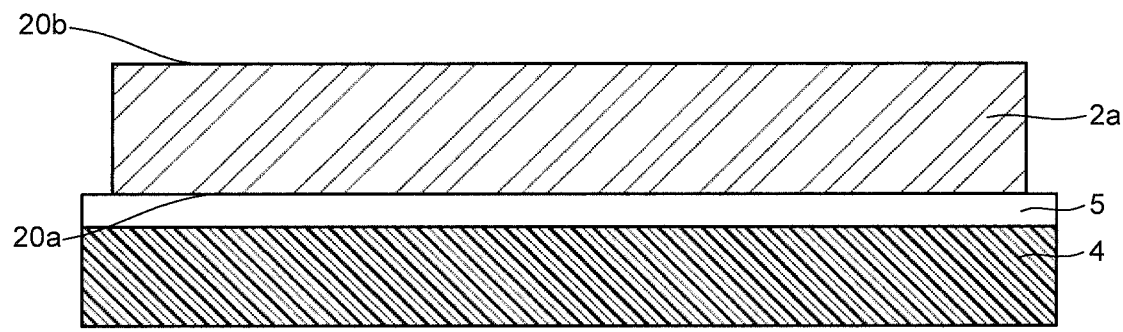
FIG. 7 is a cross-sectional view to explain an example of a method for manufacturing the scintillator array.

The first step is performed such that a scintillator material such as a sintered compact of a rare earth oxysulfide-based phosphor is cut out as a thin sheet of a predetermined size (0.5 mm or more and 2.0 mm or less in thickness), a sintered sheet 2a and the white sheet that forms the reflective layer 4 are adhered and laminated via the adhesive layer 5 such as the epoxy resin, as illustrated in FIG. 7.

Figure 8:
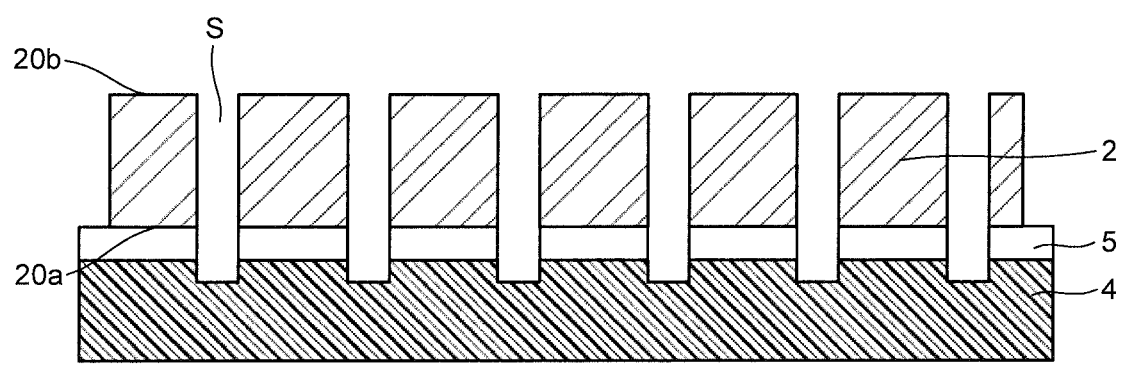
FIG. 8 is a cross-sectional view to explain the example of the method for manufacturing the scintillator array.

Next, a second step is performed such that the sintered compact 2a is subjected to grooving through dicing to partially remove the sintered compact 2a, and thereby the scintillator segments 2 and grooves S are formed, as illustrated in FIG. 8. In a cross-section of the sintered compact 2a in a thickness direction, a width of the groove S is, for example, in a range of 40 μm or more and 200 μm or less. The grooves S extend into the reflective layer 4 through the sintered compact 2a and adhesive layer 5.

Figure 9:
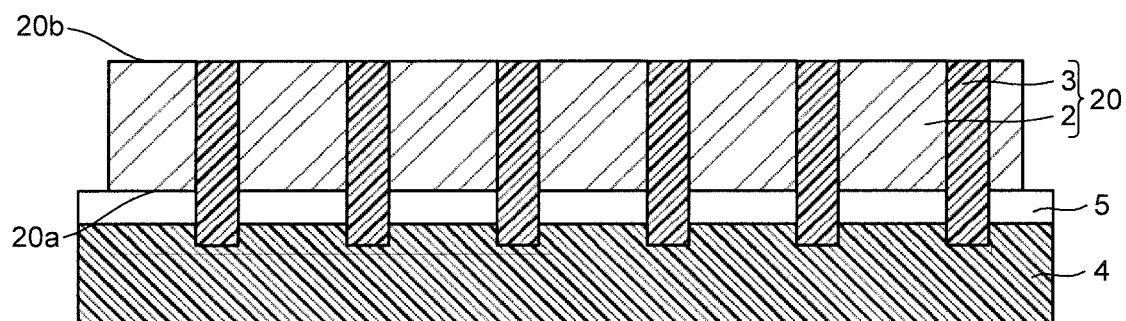
FIG. 9 is a cross-sectional view to explain the example of the method for manufacturing the scintillator array.

Next, a third step is performed to form the reflective layer 3 in the grooves S formed in the second step, as illustrated in FIG. 9. First, the reflective particles and a resin composition in an uncured state that constitutes the light transmissive resin (uncured material of the light transmissive resin) are prepared and a slurry, which is a mixture of the above, is injected into the grooves S.

The resin composition in the uncured state preferably has a viscosity of 0.2 Pa·s or more and 1.0 Pa·s or less (200 cps or more and 1000 cps or less). When the viscosity of the resin composition is larger than 1.0 Pa·s, flowability becomes poor and workability of injecting the resin composition into the grooves S decreases. When the viscosity of the resin composition is less than 0.2 Pa·s, the flowability becomes too high, resulting in lowering of applying performance or filling performance. Further, total light transmittance of the light transmissive resin is preferably 85% or more. When the total light transmittance of the light transmissive resin is less than 85%, the reflection efficiency of the reflective layer 3 becomes more likely to decrease.

The slurry is injected into the grooves S and then the slurry is cured to form the reflective layer 3, thereby adjacent scintillator segments 2 are bonded and integrated to form the structure 20. The curing processing of the slurry is appropriately set according to types or the like of the resin composition in the uncured state and a curing agent. For example, in the case of a thermosetting resin composition, a curing reaction is promoted by performing heat treatment. In the case of a resin composition such as a two-component epoxy resin, the curing reaction may be promoted by leaving it at room temperature.

Figure 10:
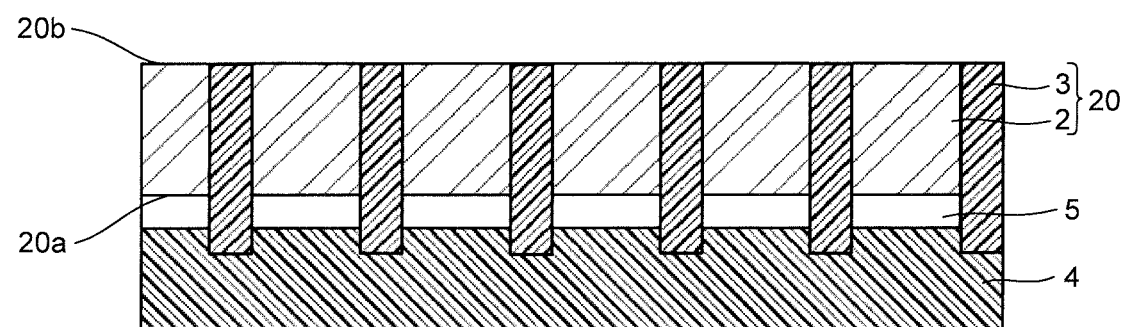
FIG. 10 is a cross-sectional view to explain the example of the method for manufacturing the scintillator array.

Next, a fourth step is performed to conduct peripheral edge processing to remove unnecessary parts of a peripheral edge of the structure 20 and further polishing, as illustrated in FIG. 10. The scintillator array 1 can be manufactured through the above steps.

(Radiation Detector)

Figure 11:
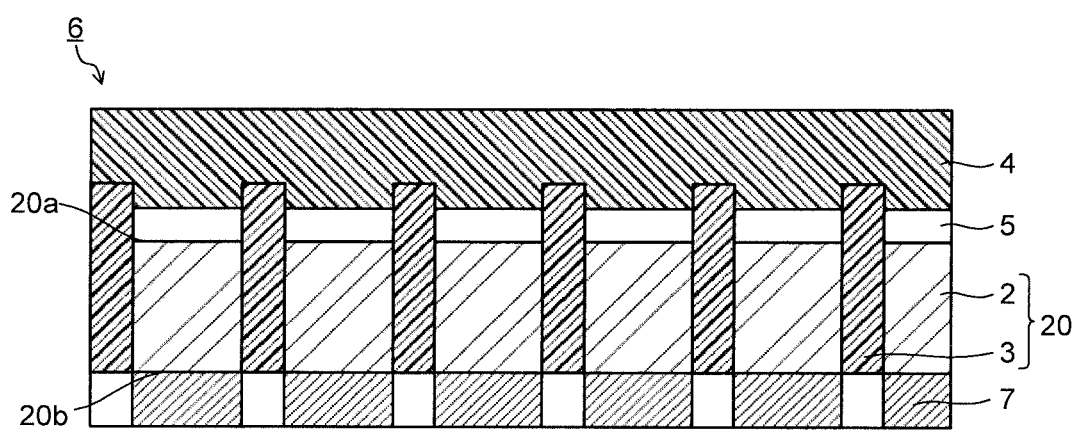
FIG. 11 is a view illustrating a constitutional example of a radiation detector.

A radiation detector of an embodiment includes the scintillator array 1 as a fluorescence generator that emits light according to incident radiation rays and further includes a photoelectric converter that receives light from the fluorescence generator and converts light output to electric output. FIG. 11 is a view illustrating a constitutional example of the radiation detector and illustrates an X-ray detector. An X-ray detector 6 illustrated in FIG. 11 includes the scintillator array 1 as the fluorescence generator and photoelectric conversion elements 7 as the photoelectric converter.

The X-ray detector 6 includes the photoelectric conversion elements 7 that are integrally provided on the surface 20b of the structure 20. The photoelectric conversion elements 7 detect light (visible light) formed by converting X-rays at the scintillator segments 2. Examples of the photoelectric conversion element 7 include a photodiode. The photoelectric conversion elements 7 are arranged to correspond to the scintillator segments 2, respectively. These components constitute the radiation detector.

(Radiation Inspection Device)

A radiation inspection device of the embodiment includes a radiation source that emits radiation rays toward an inspection target, and a radiation detector that detects the radiation rays transmitted through the inspection target. For the radiation detector, the radiation detector of the embodiment can be used.

Figure 12:
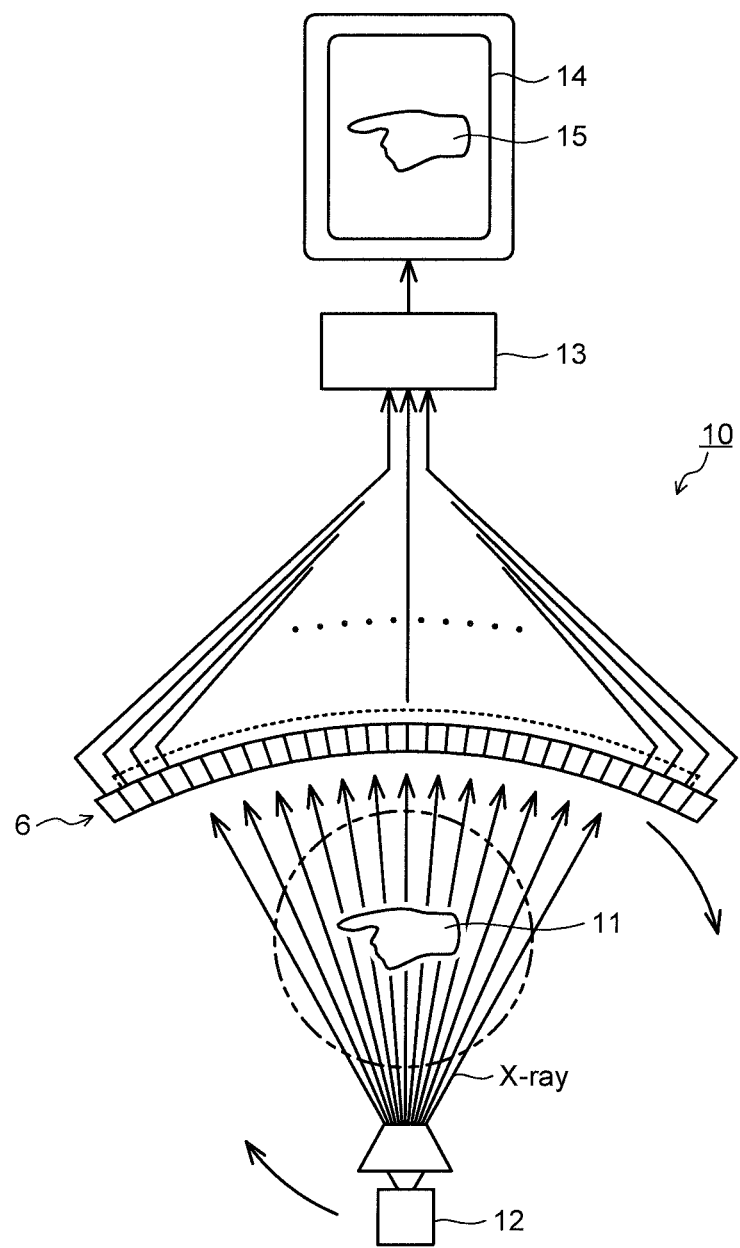
FIG. 12 is a view illustrating a constitutional example of a radiation inspection device.

FIG. 12 is a view illustrating a constitutional example of the radiation inspection device. FIG. 12 illustrates an X-ray CT scanner 10, a specimen 11, an X-ray tube 12, a computer 13, a display 14, and a specimen image 15. The X-ray CT scanner 10 includes the X-ray detector 6. The X-ray detector 6 is attached to, for example, an inner wall surface of a cylinder where an imaging portion of the specimen 11 is arranged. At an almost center of an arc of the cylinder where the X-ray detector 6 is attached, the X-ray tube 12 that emits X-rays is placed. The specimen 11 is arranged between the X-ray detector 6 and the X-ray tube 12. On an X-ray incident surface side of the X-ray detector 6, a not-illustrated collimator is provided.

The X-ray detector 6 and the X-ray tube 12 are configured to rotate around the specimen 11 while photographing with the X-rays. Image information of the specimen 11 is three-dimensionally collected from different angles. Signals obtained by X-ray photography (electric signals converted by the photoelectric conversion elements) are processed by the computer 13 and displayed on the display 14 as the specimen image 15. The specimen image 15 is, for example, a tomogram of the specimen 11. Using the scintillator array 1 in which the scintillator segments 2 are two-dimensionally arranged as illustrated in FIG. 1 also can constitute a multi-tomogram type X-ray CT scanner 10. In this case, a plurality of tomograms of the specimen 11 are photographed at the same time and, for example, a photographed result can be three-dimensionally drawn.

The X-ray CT scanner 10 illustrated in FIG. 12 includes the X-ray detector 6 including the scintillator array 1. As described above, the scintillator array 1 has excellent light output because the reflection efficiency of visible light emitted from the scintillator segments 2 is high based on the constitution of the reflective layer 3, the reflective layer 4, and the like. Using the X-ray detector 6 including the scintillator array 1 can shorten the photographing time by the X-ray CT scanner 10. This can shorten exposure time of the specimen 11 and achieve low radiation exposure. The radiation inspection device (X-ray CT scanner 10) is applicable not only to the X-ray inspection for medical diagnosis of a human body but also to the X-ray inspection for animals, the X-ray inspection for industrial usage, and so on. Further, the radiation inspection device also contributes to an improvement in inspection accuracy or the like by an X-ray nondestructive inspection device.

EXAMPLES

Concrete examples of the scintillator array 1 and their evaluation results are described.

In the examples and comparative examples, the sintered sheet 2a was fabricated as follows. Phosphor powder having a composition of $Gd_2O_2S$:Pr (Pr concentration=0.05 mol %) was temporarily molded by rubber pressing, and the temporarily molded body was degassed and sealed in a capsule made of tantalum (Ta) and then set in a hot isostatic pressing (HIP) device. The HIP device was filled with argon gas as a pressurizing medium, and the process was carried out for 3 hours under conditions of a pressure of 147 MPa and a temperature of 1425° C. In the above manner, a sintered compact in a cylindrical shape having a diameter of approximately 80 mm×a height of approximately 120 mm was fabricated. From this sintered compact, GOS ceramic plates of various sizes were cut out and used as the sintered compacts 2a for the examples and comparative examples.

Example 1

A white polyethylene terephthalate (PET) film (manufactured by Mitsubishi Chemical, 100 μm thick) with a larger area than the sintered compact 2a was bonded to a surface of a GOS ceramic plate with 76 mm in length, 25 mm in width, and 1.2 mm in thickness via an epoxy adhesive material as the adhesive layer 5. When bonding, the GOS ceramic plate, epoxy adhesive material, and white PET film were placed on top of each other and a load of 16 kg was applied and the laminate was adhered by heating at a temperature of 100° C. After cooling to room temperature, the load was removed to fabricate a laminate. The scintillator segments 2 and the grooves S were formed on the surface of the GOS ceramic plate of the laminate by grooving through dicing. A depth of the groove S was 1.25 mm. The grooves S extended into the white PET film. A slurry containing titanium oxide and epoxy resin was injected into the grooves S. The slurry was thermally cured, and surfaces of the scintillator segments 2 were polished. The peripheral edge portion was then cut and the scintillator array 1 corresponding to FIG. 4 was fabricated. The ratio D/T of the length D of the portion of the reflective layer 3 extending to the layer including the reflective layer 4 to the thickness T of the layer including the reflective layer 4 was 0.40.

Example 2

A slurry containing titanium oxide and epoxy resin was applied to the surface of the GOS ceramic plate with 76 mm in length, 25 mm in width, and 1.2 mm in thickness. The slurry was thermally cured and then polished to form the reflective layer 4 with the thickness T of 0.3 mm. Then, the scintillator segments 2 and grooves S were formed by grooving the surface of the GOS ceramic plate through dicing. The depth of the groove S was 1.25 mm. The grooves S extended into the reflective layer 4. A slurry containing titanium oxide and epoxy resin was injected into the grooves S. The slurry was thermally cured, and the surfaces of the scintillator segments 2 were polished by 0.1 mm. After that, the surface of the reflective layer 4 was polished by 0.1 mm and the peripheral edge portion was cut, and the scintillator array 1 corresponding to FIG. 3 was fabricated. The ratio D/T was 0.25.

Example 3

A slurry containing titanium oxide and epoxy resin was applied to the surface of the GOS ceramic plate with 76 mm in length, 25 mm in width, and 1.2 mm in thickness. The slurry was thermally cured and then polished to form the reflective layer 4 with the thickness of 0.3 mm. Then, the scintillator segments 2 and grooves S were formed by grooving the surface of the GOS ceramic plate through dicing. The depth of the groove S was 1.4 mm. The grooves S extended into the reflective layer 4. A slurry containing titanium oxide and epoxy resin was injected into the grooves S. The slurry was thermally cured, and the surfaces of the scintillator segments 2 were polished by 0.1 mm. After that, the surface of the reflective layer 4 was polished by 0.15 mm to penetrate the reflective layer 4 and expose the reflective layer 3 to the surface of the reflective layer 4. Then, the peripheral edge portion was cut and the scintillator array 1 was fabricated. The ratio D/T was 1.00.

Example 4

A slurry containing titanium oxide and epoxy resin was applied to the surface of the GOS ceramic plate with 76 mm in length, 25 mm in width, and 1.2 mm in thickness. The slurry was thermally cured and then polished to form the reflective layer 4 with the thickness of 0.3 mm. Then, the scintillator segments 2 and grooves S were formed by grooving the surface of the GOS ceramic plate through dicing. The depth of the groove S was 1.22 mm. The grooves S extended into the reflective layer 4. A slurry containing titanium oxide and epoxy resin was injected into the grooves S. The slurry was thermally cured, and the surfaces of the scintillator segments 2 were polished by 0.1 mm. After that, the surface of the reflective layer 4 was polished by 0.1 mm, the peripheral edge portion was cut, and the scintillator array 1 corresponding to FIG. 3 was fabricated. The ratio D/T was 0.10.

Example 5

A slurry containing titanium oxide and epoxy resin was applied to the surface of the GOS ceramic plate with 76 mm in length, 25 mm in width, and 1.2 mm in thickness. The slurry was thermally cured and then polished to form the reflective layer 4 with the thickness of 0.3 mm. Then, the scintillator segments 2 and grooves S were formed by grooving the surface of the GOS ceramic plate through dicing. The depth of the groove S was 1.35 mm. The grooves S extended into the reflective layer 4. A slurry containing titanium oxide and epoxy resin was injected into the grooves S. The slurry was thermally cured, and the surfaces of the scintillator segments 2 were polished by 0.1 mm. After that, the surface of the reflective layer 4 was polished by 0.1 mm, the peripheral edge portion was cut, and the scintillator array 1 corresponding to FIG. 3 was fabricated. The ratio D/T was 0.75.

Comparative Example 1

The GOS ceramic plate with 76 mm in length, 25 mm in width, and 1.2 mm in thickness was subjected to grooving through dicing to form the scintillator segments 2 and grooves S. A slurry containing titanium oxide and epoxy resin was injected into the grooves S. The slurry was thermally cured and then polished to form the reflective layer 3. A slurry containing titanium oxide and epoxy resin was applied to the X-ray incident surface of the structure 20, and the slurry was cured by heating at the temperature of 100° C. for three hours. The resultant was polished after cured to achieve the thickness of 150 μm to form the reflective layer 4, and the scintillator array 1 was fabricated. The reflective layer 3 did not extend to the reflective layer 4.

Comparative Example 2

The GOS ceramic plate with 76 mm in length, 25 mm in width, and 1.2 mm in thickness was subjected to grooving through dicing to form the scintillator segments 2 and grooves S. A slurry containing titanium oxide and epoxy resin was injected into the grooves S. The slurry was thermally cured and then polished to form the reflective layer 3. Next, a white PET film (manufactured by Mitsubishi Chemical, 100 μm thick) as the reflective layer 4 was bonded to the structure 20 via an epoxy adhesive material. When bonding, the structure 20, epoxy adhesive material, and white PET film were placed on top of each other, a load of 16 kg was applied, and the laminate was heated at the temperature of 100° C. for adhesion. After cooling to room temperature, the load was removed, and the scintillator array 1 was fabricated. The reflective layer 3 did not extend to the reflective layer 4.

Comparative Example 3

The GOS ceramic plate with 76 mm in length, 25 mm in width, and 1.2 mm in thickness was subjected to grooving through dicing to form the scintillator segments 2 and grooves S. A slurry containing titanium oxide and epoxy resin was injected into the grooves S. The slurry was thermally cured and then polished to form the reflective layer 3. A slurry containing titanium oxide and epoxy resin was applied to the X-ray incident surface of the structure 20 and cured by heating at the temperature of 100° C. for four hours. The resultant was polished after cured to achieve the thickness of 100 μm to form the reflective layer 4, and the scintillator array 1 was fabricated. The reflective layer 3 did not extend to the reflective layer 4.

A peeling property of the reflective layer 4 in each of the examples and comparative examples was evaluated by the following compulsory test. The obtained scintillator array 1 was placed in a constant temperature and humidity testing machine and left at a temperature of −20° C. for 30 minutes, then heated to a temperature of 60° C. at a temperature rising rate of 5° C./min, left at the temperature of 60° C. for 30 minutes, and then the temperature was lowered to −20° C. at a temperature drop rate of 5° C./min. After this cycle was performed 1000 times, the peripheral edge portion of the scintillator array 1 was observed and evaluated for the presence of peeling. A humidity in the test was 40% RH (relative humidity). The results are listed in Table 2.

TABLE 2

|  | D/T | Peeling of reflective layer 4 |
| --- | --- | --- |
| Example 1 | 0.40 | Absent |
| Example 2 | 0.25 | Absent |
| Example 3 | 1.00 | Absent |
| Example 4 | 0.10 | Partially present |
| Example 5 | 0.75 | Absent |
| Comparative Example 1 | 0 | Present |
| Comparative Example 2 | 0 | Present |
| Comparative Example 3 | 0 | Present |

Table 2 shows that the scintillator array 1 of each of the examples includes the reflective layer 3 between the scintillator segments 2, the reflective layer 3 extending and entering into the layer having the reflective layer 4 to form an integrate, resulting in a significant difference from the comparative examples observed in the peeling property of the reflective layer 4. Even when the degree of the entry of the reflective layer 3 into the reflective layer 4 was small, there was less peeling than in the comparative examples.

The scintillator array of the embodiment can practically eliminate peeling of the reflective layer 4, which used to occur at a certain rate. This elimination is industrially useful.

What is claimed is:

1. A scintillator array comprising:
a structure comprising scintillator segments and a first reflective layer, the first reflective layer being provided between the scintillator segments and being configured to reflect light, and the scintillator segments having a sintered compact containing a rare earth oxysulfide phosphor; and
a layer comprising a second reflective layer provided above the structure, the second reflective layer being configured to reflect light,
wherein the first reflective layer has a portion extending into the layer.

2. The scintillator array according to claim 1, wherein a ratio D/T of a length D of the portion of the first reflective layer to a thickness T of the layer is 0.10 or more and 1.00 or less.

3. The scintillator array according to claim 1, wherein at least one reflective layer selected from the group consisting of the first and second reflective layers contains:
a resin including at least one selected from the group consisting of epoxy resin, silicone resin, phenol resin, urea resin, melamine resin, polyester resin, polyurethane resin, and acrylic resin; and
reflective particles having at least one selected from the group consisting of titanium oxide, aluminum oxide, silicon oxide, barium sulfate, zinc oxide, zirconium oxide, and silicon oxide, the reflective particles being configured to reflect light.

4. The scintillator array according to claim 1, wherein the layer further has an adhesive layer, and
the second reflective layer is provided above the structure via the adhesive layer.

5. The scintillator array according to claim 4, wherein the portion extends into the adhesive layer and does not extend to the second reflective layer.

6. The scintillator array according to claim 4, wherein the adhesive layer contains at least one resin selected from the group consisting of epoxy resin, silicone resin, phenol resin, urea resin, melamine resin, polyester resin, polyurethane resin, polyolefin resin, and acrylic resin.

7. The scintillator array according to claim 6, wherein the adhesive layer further contains at least one selected from the group consisting of titanium oxide, zirconium oxide, aluminum oxide, and silicon oxide.

8. The scintillator array according to claim 1, wherein the rare earth oxysulfide phosphor has a composition represented by
a general formula $RE_2O_2S:Pr$
where in the formula, RE denotes at least one element selected from the group consisting of Y, Gd, La and Lu, and a content of Pr to a content of $RE_2O_2S$ is 0.001 mol % or more and 10 mol % or less.

9. A radiation detector comprising the scintillator array according to claim 1.

10. A radiation inspection device comprising the radiation detector according to claim 9.

11. A method for manufacturing a scintillator array, comprising:
bonding a sintered sheet and a layer, the sintered sheet containing a rare earth oxysulfide phosphor, and the layer comprising a second reflective layer, the second reflective layer being configured to reflect light;
partially removing the sintered sheet to form scintillator segments and a groove, the groove being provided between the scintillator segments and extending into the layer;
injecting a slurry containing a resin and reflective particles into the groove, reflective particles being configured to reflect light; and
curing the slurry to form a first reflective layer.

* * * * *